(12) United States Patent
Prybella et al.

(10) Patent No.: US 7,055,401 B2
(45) Date of Patent: Jun. 6, 2006

(54) CLOSED METHOD AND SYSTEM FOR THE SAMPLING AND TESTING OF FLUID

(75) Inventors: John R. Prybella, Marshfield, MA (US); Susan Roberts, Natick, MA (US); Jose Luyo, Brockton, MA (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 10/801,180

(22) Filed: Mar. 15, 2004

(65) Prior Publication Data

US 2005/0199077 A1 Sep. 15, 2005

(51) Int. Cl.
*G01N 1/00* (2006.01)
(52) U.S. Cl. .................................. 73/863.23
(58) Field of Classification Search ............. 73/864.63, 73/864.65, 863.23, 863.71, 863.72, 863.73
See application file for complete search history.

(56) References Cited

U.S. PATENT DOCUMENTS

| | | | | |
|---|---|---|---|---|
| 3,858,573 | A | * 1/1975 | Ryan et al. ................. 600/543 |
| 4,256,120 | A | 3/1981 | Finley .......................... 128/764 |
| 4,296,759 | A | 10/1981 | Joslin et al. ................. 128/766 |
| 4,590,810 | A | * 5/1986 | Hunkin et al. ............ 73/864.63 |
| 4,625,574 | A | * 12/1986 | Robbins .................... 73/864.63 |
| 4,658,655 | A | * 4/1987 | Kanno ....................... 73/863.85 |
| 4,749,658 | A | * 6/1988 | Jaekel et al. ................ 436/180 |
| 5,496,301 | A | 3/1996 | Hlavinka et al. ............ 604/409 |
| 5,538,690 | A | * 7/1996 | Greer et al. .................. 422/86 |
| 5,552,118 | A | 9/1996 | Mayer ......................... 422/103 |
| 5,928,166 | A | 7/1999 | Shemesh et al. ............ 600/576 |
| 6,152,901 | A | 11/2000 | Arruego et al. ............. 604/195 |
| 6,156,019 | A | 12/2000 | Langevin .................... 604/323 |
| 6,387,086 | B1 | 5/2002 | Mathias et al. ............. 604/409 |
| 6,543,302 | B1 | * 4/2003 | Pratt ......................... 73/864.63 |

OTHER PUBLICATIONS

*ITL Corporation Product—Samplok® Sampling Kit (SSK)* Product information from ITL Corporation Product catalog, available on-line (internet) through URL: www.itlcorporation.com/level2/frames/products/i_ssk.htm Includes 2 pages of catalog description and a 1 page PDF file. On-line information available as of Mar. 31, 2004. Earliest date available is unknown.

*Gambro BCT—Example Standard Operating Procedure: Sampling Platelet Products Using the Tima® Accel® Enhanced Platelet, Plasma RBC Set Catalog #80440,80449 And/Or Blood Component Sampling Set Catalog # 70051,* Gambro BCT, Inc. 8 pages. Date available: copyright notice for the catalog entry provides date of first publication as 2005. Earliest date available is unknown.

(Continued)

Primary Examiner—Robert Raevis

(57) ABSTRACT

A closed fluidic sampling system. The system includes a first port for receiving a sample of fluid and a sampling chamber in fluid communication with the first port. A a one-way valve allows fluid to flow from the first port towards the sampling chamber while preventing backflow of fluid towards the first port. A second port in fluid communication with the sampling chamber enables fluid to be withdrawn from the sampling chamber. The fluid may be a blood component, such as platelets, plasma, whole blood, or red blood cells.

71 Claims, 3 Drawing Sheets

OTHER PUBLICATIONS

*Charter Medical—Platelet Sampling Devices*, Product information from Charter Medical Ltd. Product catalog, available on-line (internet) through URL: www.chartermedical.com/products_catolog-detail.cfm?PID=73&cid=79 Includes 6 pages of catalog description. On-line information available as of Mar. 15, 2004. Copyright notice on the on-line catalogue section indicates first publication dates of 1998-2004. Earliest date available is unknown.

* cited by examiner

CLOSED METHOD AND SYSTEM FOR THE SAMPLING AND TESTING OF FLUID

FIELD OF THE INVENTION

The present invention generally relates to a system and method for obtaining a sample of a fluid from a fluid source, such as a blood product, and performing testing on the sample of fluid, while reducing the risk of contamination.

TECHNICAL FIELD AND BACKGROUND ART

Currently, the greatest infectious risk associated with blood transfusion is a septic reaction from bacterially contaminated blood products. In particular, platelets are very vulnerable to bacterial contamination since, after donation, they are typically kept at relatively warm temperatures that facilitate rapid bacterial growth. Approximately one in every 2000 platelet units are bacterially contaminated, and one in 50,000 bags result in a septic death. The risk of receiving a bacterially contaminated unit is currently higher than the risk of receiving a unit that is contaminated with a virus, such as HIV. Compounding this problem is that patients requiring platelet transfusion often have weakened immune systems, further increasing the risk of infection if contaminated platelets are introduced.

To deal with this problem, several European countries have adopted procedures for bacterial screening of platelets. Additionally, in the United States, the American Association of Blood Banks recently issued guidelines recommending that all platelet products be tested for bacteria.

To test the blood product contained in the blood product bag, it is often necessary to remove a small sample of the blood product from the blood product bag. This may be accomplished by attaching a syringe to the blood product bag. By manipulating the syringe, a measured sample of the blood product can then be drawn into the tube. This methodology has several drawbacks. The syringe inherently contains air, which may contaminate the sample or flow into the blood product bag and contaminate the blood product. Additionally, withdrawn sample contaminated by bacteria or other contaminants in the syringe may backflow back into the blood product bag, or be intentionally pushed back into the blood product bag if too much sample is initially withdrawn. Another disadvantage of the syringe is that it is awkward to manipulate.

Alternatively, a sample of the blood product may be removed from the blood product bag by connecting an evacuated, flexible sample bag to the blood product bag. Upon feeding the sample into the bag via gravity, the bag expands. In addition to allowing backflow back into the blood product bag, this methodology includes the drawback that it is difficult to acquire a precise amount of sample in the sample bag, since the bag does not consistently return to a predefined volume upon expanding.

SUMMARY OF THE INVENTION

A closed fluidic sampling system and method for easily obtaining and transferring a precisely metered sample of fluid from a fluid source to a test vial, is provided. In accordance with one aspect of the invention, the system includes a first port for receiving a sample of fluid, and a sampling chamber in fluid communication with the first port. A one-way valve allows fluid to flow from the first port towards the sampling chamber, while preventing backflow of fluid towards the first port. Thus, the system advantageously prevents fluid and other contaminants in the sampling system from entering and adversely affecting the fluid source. A second port in fluid communication with the sampling chamber enables the sample fluid to be withdrawn from the sampling chamber.

In a related embodiment of the invention, the second port may be closed and capable of being attached to a first container by a sterile connection device. In another related embodiment the second port may include a hollow spike. The hollow spike has a piercing end for piercing a septum of a first container, which may be a test vial.

In further related embodiments of the invention, the system may include a connector, which may be a Y-connector. First tubing is coupled at one end to the first port and at another end to the connector. Second tubing is coupled at one end to the sampling chamber and at another end to the connector. Third tubing is coupled at one end to the second port and at another end to the connector, wherein the connector is a Y-connector. The one-way valve may be positioned within the first tubing.

In further related embodiment of the invention, the system may include a gas vent in fluid communication with the sampling chamber, the gas vent for venting gas displaced by the sample. The gas vent may include a filter so as to maintain a closed system. A clamp may be used to further control flow of fluid entering from the first port. The first port may be attached to a second container that may be, for example, a blood product bag that contains platelets, whole blood, red cells, or plasma. In other embodiments, the first port may be initially closed or attached to a gas vent, and capable of being attached to a second container by a sterile connection device.

In accordance with another aspect of the invention, a closed fluidic sampling system includes a sampling chamber. A first conduit is in fluid communication with the sampling chamber, the first conduit for receiving a sample of fluid. A one-way valve disposed in the first conduit allows fluid to flow downstream towards the sampling chamber while preventing backflow of fluid from the sampling chamber. The system further includes withdrawal means for enabling withdrawal of fluid from the sample chamber.

In related embodiments of the invention, the withdrawal means may include a hollow spike in fluid communication with the sample chamber, the hollow spike including a piercing end. The piercing end may be covered by a removable cap to prevent exposure and accidental damage. The system may include a first container, such as a test vial, that may include, for example, a septum capable of being pierced by the piercing end of the hollow spike. The first container may be evacuated prior to being pierced by the piercing end of the hollow spike. A connector, which may be a Y-connector, enables fluid communication between the first conduit, the hollow spike, and the sample chamber.

In further related embodiments of the invention, the withdrawal means may include a second conduit in fluid communication with the sample chamber, the second conduit positioned downstream from the one-way valve. The second conduit may be coupled to a hollow spike, or may be closed at a first end, the first capable of being attached to a first container by a sterile connection device. A connector, such as a Y-connector, may enable fluid communication between the first conduit, the second conduit, and the sample chamber.

In still further related embodiments of the invention, the first conduit may be sealed at a first end, the first end upstream from the one-way valve and capable of being attached to a second container by a sterile connection device.

The first conduit may be in unitary construction with, and attached at a first end to, a second container, the first end upstream from the one-way valve. The second container may be a blood product bag that contains platelets, whole blood, red cells, or plasma. In other embodiments, the first conduit may be attached at a first end to a gas vent, the gas vent including a filter, the first end upstream from the one-way valve.

In yet further related embodiments of the invention, a gas vent may be in fluid communication with the sampling chamber, the gas vent for venting gas displaced by the sample. A filter may be positioned between the sampling chamber and the gas vent. A clamp may be used to further control flow of fluid entering from the first port.

In accordance with another aspect of the invention, a method for obtaining a sample of a fluid from a fluid source is provided. The method includes introducing the fluid through a first port in fluid communication with the fluid source. Fluid is allowed to flow from the first port towards a sampling chamber while backflow of fluid towards the first port is prevented. Fluid from the sampling chamber is withdrawn via a second port into, for example, a test vial.

In related embodiments of the invention, the fluid withdrawn from the sampling chamber may be tested. Testing may include bacterial detection and/or cell counting. The first port may be in unitary construction with, and attached to, the fluid source. The first port may be sealed, and introducing the fluid may include attaching the first port to the fluid source using a sterile connection device. Attaching the first port to the fluid source may include applying heat and/or a radio frequency to the first port. A one-way valve may be positioned between the first port and the sampling chamber.

In further related embodiments of the invention, the sampling chamber may be flexible and resilient. Introducing the fluid into the first port may include squeezing the sampling chamber to create a vacuum, followed by releasing the sampling chamber to create a vacuum in the sampling chamber. The gas displaced from the fluid entering the sampling chamber may be vented. Introducing the fluid into the first port may include opening a clamp that controls flow of fluid through the first port.

In other related embodiments of the invention, the fluid source may be a blood component bag. The fluid may be platelets, whole blood, red cells, or plasma. The second port may initially be closed, or include a hollow tube in fluid communication with the sampling chamber. The hollow tube may include a piercing end for piercing a septum of the sample vial. The sample vial may include an evacuated volume forming a vacuum, the method further comprising drawing the fluid from the sample chamber into the sample vial due to the vacuum.

In embodiments related to the above-described embodiments, the sampling chamber may include indicia for indicating a predetermined volume of fluid within the system or sampling chamber. The indicia allows the operator to precisely meter the amount of sample fluid obtained from the fluid source.

The sampling chamber may be made of a flexible and resilient material. This allows the sampling chamber to be squeezed so as to expel fluid from the sampling chamber, and further released so as to create a vacuum that can be used to draw the sample fluid from the fluid source. Upon releasing the squeezed sampling chamber, the sampling chamber may return to a predetermined volume. In other embodiments, the sampling chamber may be made of a rigid material, wherein sample fluid from the fluid source can be fed by gravity into the sampling chamber.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, the following terms shall have the meanings indicated, unless the context otherwise requires:

The term "a closed fluidic sampling system" as used herein shall refer to a functionally closed fluidic sampling system sealed to ensure fluid sterility by hermetically sealing the entire system or by providing sterile barrier filters at all connections to the sampling system.

The term "blood product" as used herein shall include whole blood or any of its component(s), such as, without limitation, erythrocytes, leukocytes, platelets and plasma, either alone or in combination.

In illustrative embodiments, a closed fluidic sampling system and method for transferring a precisely metered sample of fluid from a fluid source to a desired destination is presented. Generally, the system includes a one-way valve that allows for collection of a sample of fluid from a fluid source to a sampling chamber via a first port, while preventing backflow of fluid or other contaminants into the fluid source. The obtained sample is transferred from the sampling chamber to the desired destination via a second port. The desired destination may be a container used in conducting various tests on the sample of fluid. Details are discussed below.

Figure 1:
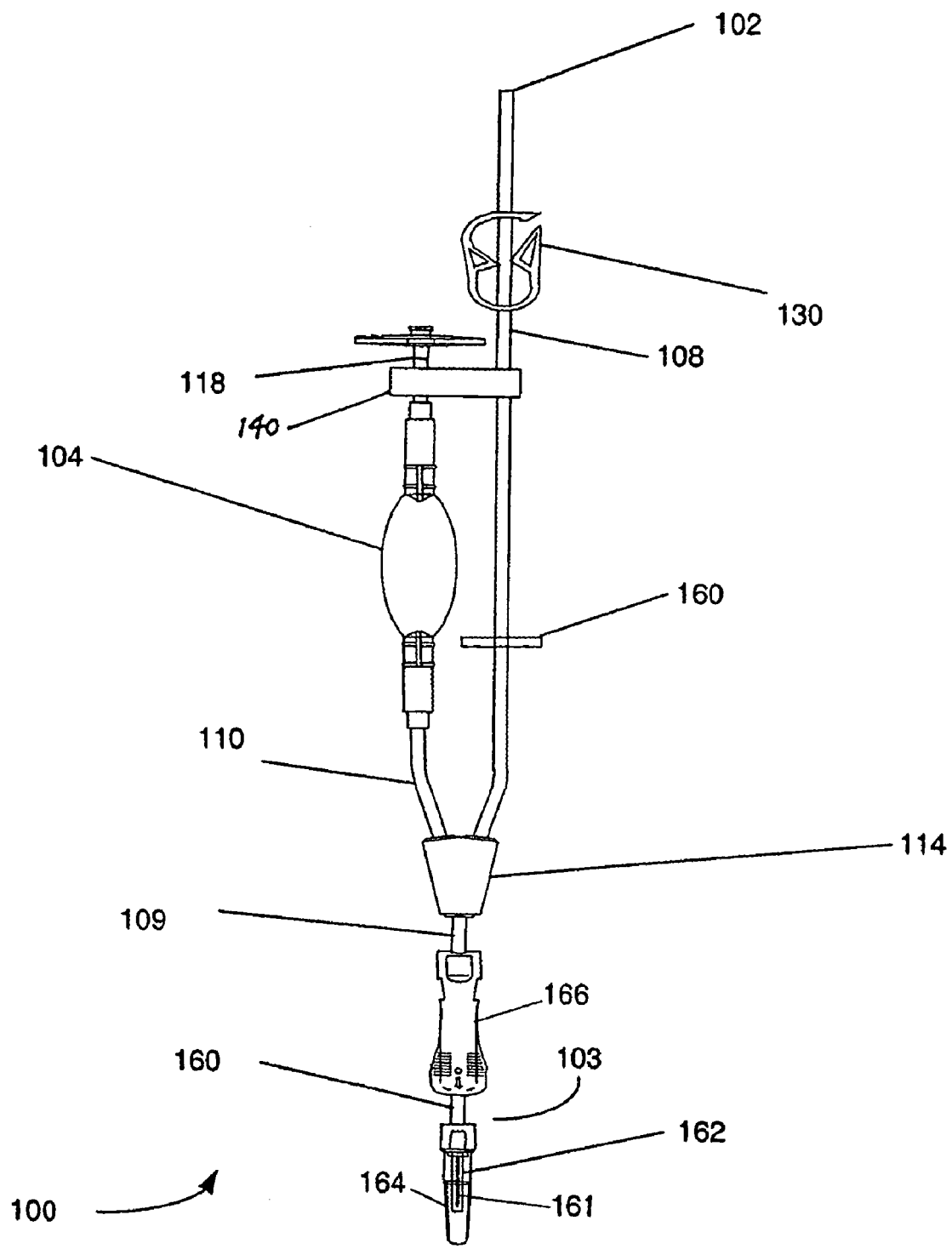
FIG. 1 is a diagram illustrating a closed fluidic sampling system, in accordance with one embodiment of the invention.

FIG. 1 is a diagram illustrating a closed fluidic sampling system 100, in accordance with one embodiment of the invention. The system 100 includes a first port 102 and a second port 103 that are in fluid communication with a sampling chamber 104. The first port 102 is capable of being attached to a blood product bag, such that a sample of blood product can be transferred to the sampling chamber 104. The second port 103 allows for removal of sample from the sampling chamber 104.

The first port 102 is in fluid communication with the sampling chamber 104 via at least a first conduit 108. In various embodiments, the first conduit 108 may include an inlet at one end that defines the first port 102. The inlet may be made of a plastic or other suitable material that allows the first port 102 to be attached to the blood product bag in a sterile manner using a Sterile Connection Device (SCD). The SCD may use, without limitation, radio frequency waves and/or heat in attaching the first port 102 to the blood product bag.

Prior to attaching the first port 102 to the blood product bag, the first port 102 may be closed so that contaminants cannot enter the system 100. Alternatively, the first port may include a gas vent that may be advantageously used to sterilize the system 100 prior to use. This may be accomplished, for example, by passing a sterilization fluid, such as ethylene oxide, through the gas vent into the conduit 108. To prevent unwanted contaminants from entering the system 100, the gas vent may include a filter and/or be selectively opened using a clamp.

In accordance with one embodiment of the invention, a one-way valve 160 is disposed in the first conduit 108. The one-way valve 160 may be of various types known in the art, such as, without limitation, a check valve or a flap valve. The one-way valve 160 allows fluid to flow towards the sampling chamber 104, while preventing accidental or intentional backflow of fluid from the sampling chamber 104 towards the fluid source. Fluid downstream from the one-way valve 160, which may contain bacteria, microorganisms or other contaminants, is thus prevented from entering and adversely affecting the fluid source. Fluid prevented from back flowing into the fluid source may include, without limitation, air originally present in the system 100 and/or sample fluid already obtained from the fluid source.

As illustrated in the embodiment of FIG. 1, the first conduit 108 is connected to a three-way connector 114. The three-way connector is further connected to the second port 103 and the sampling chamber 104 via a second conduit 109 and a third conduit 110, respectively. While the fluid flow in the first conduit 108 is unidirectional due to the one-way valve 160, the flow in the third conduit 110 is capable of flowing bidirectionally. Fluid in the third conduit 110 can thus flow towards the sampling chamber 104 when a sample of fluid is being loaded, and away from the sampling chamber 104 when the sample fluid is delivered to the desired destination via the second port 103.

The three-way connector 114 may be integrally formed so as to define, without limitation, a "Y" or "T" connector. It will be recognized that the three-way connector 202 may also be formed of a series of components that are assembled to provide the branched fluid flow path defined by connector 114. Instead of a three-way connector, other embodiments are also foreseeable. For example, the first port 102 may be connected directly to the sampling chamber 104 via the first conduit 108, while the second port 103 is connected directly to the sampling chamber 104 via a different conduit.

The sampling chamber 104 may include, or otherwise be in fluid communication with, a gas vent 118. Gas displaced by sample fluid entering the sampling chamber 104, and/or any sterilization fluid pumped through the system 100, can be vented through the gas vent 118. The gas vent 118 may include a filter such as, but not limited to, a bacterial filter. The filter prevents introduction of contaminants from the outside environment into the system 100, thus helping to maintain a closed fluidic sampling system. The gas vent 118 may be selectively connected to the sampling chamber 104 via, for example, a suitable valve or clamp 140.

Figure 2:
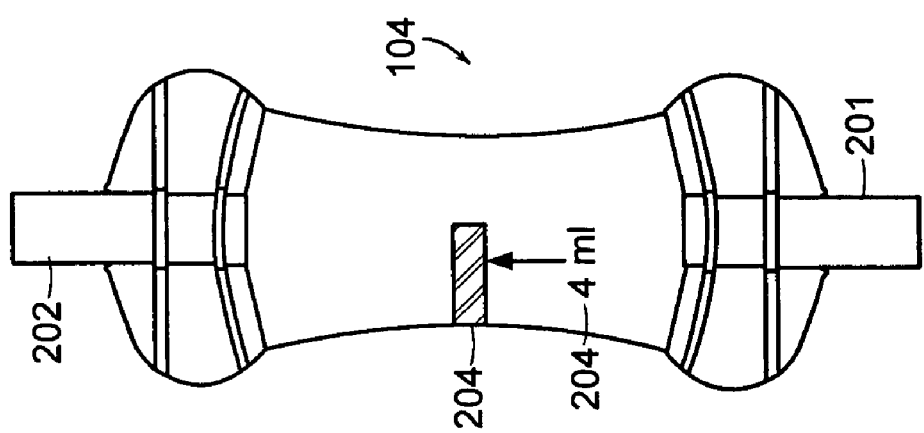
FIG. 2 is a diagram illustrating a sampling chamber, in accordance with one embodiment of the invention.

FIG. 2 is a diagram illustrating the sample chamber 104 in more detail, in accordance with one embodiment of the invention. The sampling chamber 104 includes a first port 201 that allows fluid sample to flow into and out of the sampling chamber 104. Additionally, the sampling chamber 104 may also include a second port 202, which may be coupled to a gas vent 118, as discussed above with reference to FIG. 1.

The sampling chamber 104 may be made of a rigid material, such as, but not limited to, a rigid plastic. Loading of a sample of fluid into the rigid sampling chamber 104 may be based, for example, on gravity, with the fluid source positioned higher than the sampling chamber 104. A sample of fluid can be obtained by opening a clamp 130 (see FIG. 1), which allows fluid to flow by gravity from the first port 102 through the first and third conduit 108 and 110 and into the sampling chamber 104. In various embodiments, gas trapped in the second conduit 109 prevents flow of fluid into second conduit 109. Gas displaced by fluid entering the sampling chamber 104 can exit the sampling chamber 104 through open gas vent 118. Upon filling the sampling chamber 104 to the desired level, the clamp 130 is closed to prevent further sample fluid from entering into the system 100 via the first port 102; and the clamp 140 to the gas vent 118 is closed to prevent gas from the external environment from entering the sampling chamber 104.

In other embodiments, the sampling chamber 104 can be made of a flexible and resilient material, which may be, for example, a soft plastic such as Polyvinyl Chloride (PVC). The sampling chamber 104 is typically resilient such that upon releasing the squeezed sampling chamber 104, the sampling chamber 104 returns to a predefined volume when at a resting state. Loading of the flexible and resilient sampling chamber 104 can be accomplished by first squeezing the sampling chamber 104 to expel any gas in the sampling chamber 104 through the open gas vent 118. Upon expelling the gas, the clamp 140 to the gas vent 118 is closed to prevent gas from reentering the sampling chamber 104, and the sampling chamber 104 released, such that the sampling chamber 104 reverts back to its former shape (i.e., the predefined volume). An area of low pressure is thus created in the sampling chamber 104, which causes a sample of fluid to be drawn from the first port 102 into the sampling chamber 104. Since the sampling chamber 104 returns to its former shape and associated predefined volume, a precise amount of fluid can be drawn from the fluid source. After drawing the sample fluid into the sampling chamber 104, the clamp 130 can be closed to prevent further sample fluid from entering into the system 100 via the first port 102.

The sampling chamber 104 may include various indicia 204 for aiding an operator of the system 100 in obtaining a desired amount of sample fluid from the fluid source. Obtaining a precise amount of sample fluid may advantageously ensure a minimum volume required for effective tests, and/or limit over collecting which would reduce the efficacy of the blood product contained in the blood product bag.

The indicia 204 may include at least one line or other marking that corresponds to a level to which the sampling chamber 104 can be desirably filled. The indicia 204 may also include a symbol or descriptive text associated with the marking that indicates the volume of sample obtained. The indicated volume may correspond to the volume of fluid within the sample chamber. Alternatively, the indicated volume may correspond to the volume of fluid downstream from the one-way valve 160.

Transferring a desired amount of sample fluid into the sample chamber 104 can be accomplished by opening clamp 130, and comparing the amount of fluid entering the sampling chamber 104 with the desired volume level marked by the indicia 204. Upon the sample fluid reaching the marked volume level, the flow of fluid through the first port 102 is stopped by closing clamp 130.

After the sample of fluid has been collected in the sampling chamber 104, the sample of fluid can be transferred to the desired destination via the second port 103. The transfer of sample fluid from the system 100 to the desired destination may occur while the first port 102 is still attached to the blood product bag. Alternatively, the first port 102 can be disconnected from the blood product bag prior to transferring the sample fluid to the desired destination. To disconnect the first port 102 from the blood product bag in a closed, sterile manner, various methods known in the art may be used, such as, without limitation, heat sealing and/or fastening grommets onto, and cutting, conduit 108.

As illustrated in the embodiment of FIG. 1, the second port 103 is coupled to the sampling chamber 104 via the second conduit 109, the three-way connector 114, and the third conduit 110. In various embodiments, the second conduit 109 may include an inlet at one end that defines the second port 103. Prior to attaching the second port 103 to the desired destination, the inlet defining the second port 103 may be closed and made of plastic or other suitable material, such that a SCD can be used to attach the second port 103 to the desired destination in a sterile manner.

In other embodiments, the second port 103 may include a hollow spike 161 in fluid communication with the second conduit 109 and defining at least one passageway through which fluid may flow. To prevent sample fluid from exiting the spike 161 prior to the transfer of sample fluid from the sampling chamber 104, the spike 161 may be encapsulated in a elastomeric sheath 162 that can be pierced by the spike 161 when fluid transfer is desired. Alternatively, or in combination with an elastomeric sheath 162, a clamp may be positioned, without limitation, on the second conduit. The spike 161 may also be covered by a cap 164 that provides protection against accidental contact with spike 161.

The desired destination may be, without limitation, a container of various size, shape, and utility. Upon connecting the second port 103 to the container, gravity may be used to transfer the sample from the system 100 to the container, with the system 100 positioned higher than the container. In embodiments where the sampling chamber 104 is flexible, the sampling chamber 104 may also be squeezed, such that the sample fluid is urged out of the second port 103.

Figure 3:
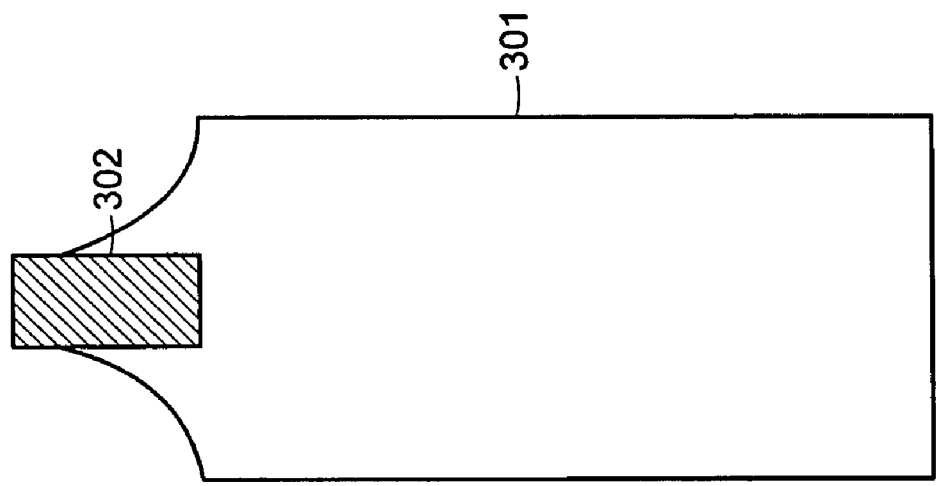
FIG. 3 (prior art) is a diagram of an evacuated vial that includes a septum.

In various embodiments, the container may be a vial that can be used while testing the sample fluid. The vial 301 may include, without limitation, a septum 302, as shown FIG. 3 (prior art). The vial 301 may be evacuated, such that when the hollow spike 161 of system 100 pierces the septum 302, the sample fluid contained in the system 100 is drawn by the vacuum into the vial 301.

After transferring the sample fluid from the sampling chamber 104 to the desired destination, a needle guard 166 may be slid down the second conduit 109 so as to cover the hollow spike 161. In various embodiments, the needle guard 166 may clip or snap over the hollow spike 161 so as to lock the needle guard 166 in place over the hollow spike 161 effectively preventing the system 100 from being used again.

Figure 4:
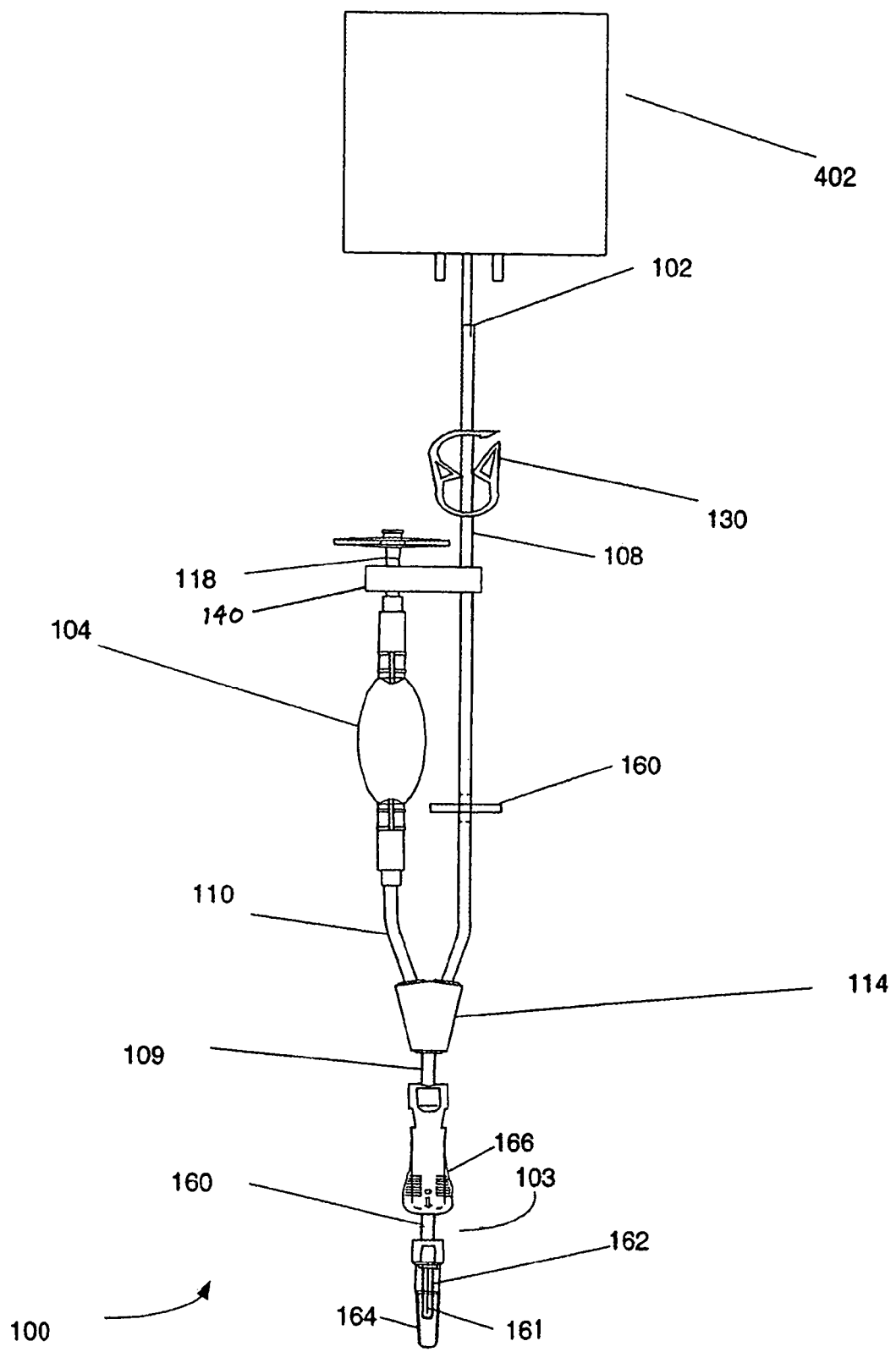
FIG. 4 is a diagram illustrating a closed fluidic sampling system in unitary construction with a blood product bag, in accordance with one embodiment of the invention.

FIG. 4 is a diagram illustrating the closed fluidic sampling system 100 of FIG. 1 in unitary construction with a blood product bag 402, in accordance with one embodiment of the invention. Preconnecting first port 102 to the blood product bag 402 eliminates the need to make a sterile connection, thereby removing a possible compromise in sterility, and reducing cost and labor.

Components of the system 100 are preferably made of a medical grade plastic material. Medical grade materials include, without limitation, polyvinyl chloride, polyester, polyurethane, polyolefin, or a blend of these materials. The system is not limited to these materials however, and other materials may be used, particularly in those embodiments where compatibility with the sampled fluid is not an issue.

The above-described embodiments can be used to transfer an accurately metered sample of any blood product or component without negatively affecting the fluid source. While ideal for transferring a platelet sample for bacterial detection, the above-described embodiments can be used for whole blood, red cells, plasma or other fluids. Testing to be performed on the metered is not limited to bacterial detection. For example, cellular counts and testing may be performed.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A closed fluidic sampling system comprising:
   a first port for receiving a sample of fluid;
   a sampling chamber in fluid communication with the first port;
   a one-way valve for allowing fluid to flow from the first port towards the sampling chamber while preventing backflow of fluid towards the first port;
   a second port in fluid communication with the sampling chamber, the second port for withdrawing fluid from the sampling chamber and,
   a gas vent with a filter in fluid communication with the sampling chamber, the gas vent for venting gas displaced by the sample.

2. The system according to claim 1, wherein the second port includes a hollow spike, the hollow spike having a piercing end for piercing a first container.

3. The system according to claim 1, wherein the second port is closed and is capable of being attached to a first container by a sterile connection device.

4. The system according to claim 1, further comprising:
   a connector;
   first tubing coupled at one end to the first port and at another end to the connector;
   second tubing coupled at one end to the sampling chamber and at another end to the connector; and
   third tubing coupled at one end to the second port and at another end to the connector.

5. The system according to claim 4, wherein the connector is a Y-connector.

6. The system according to claim 4, wherein the one-way valve is positioned within the first tubing.

7. The system according to claim 1, wherein the sampling chamber includes indicia for indicating a predetermined volume of fluid within the sample chamber.

8. The system according to claim 1, wherein the sampling chamber includes indicia for indicating a predetermined volume of fluid within the system.

9. The system according to claim 1, wherein the first port is closed and is capable of being attached to a second container by a sterile connection device.

10. The system according to claim 9, wherein the second container is a blood product bag.

11. The system according to claim 1, further comprising a second container in fluid communication with the first port.

12. The system according to claim 11, wherein the second container is a blood product bag.

13. The system according to claim 1, wherein the first port is in communication with the gas vent.

14. The system according to claim 1, wherein the sampling chamber is made of a flexible and resilient material.

15. The system according to claim 14, wherein the sampling chamber defines a pre-determined volume when in a resting state.

16. The system according to claim 14, wherein the sampling chamber is capable of being squeezed so as to expel fluid from the sampling chamber, and further released so as to create a vacuum for acquiring the sample fluid.

17. The system according to claim 16, wherein after being released, the sampling chamber returns to a predetermined volume.

18. The system according to claim 1, wherein the sampling chamber material is made of a rigid material.

19. The system according to claim 1, wherein the one-way valve prevents backflow of at least one of air and liquid.

20. The system according to claim 1, further comprising a clamp for controlling flow of fluid entering from the first port.

21. A closed fluidic sampling system comprising:
    a sampling chamber;
    a first conduit in fluid communication with the sampling chamber, the first conduit for receiving a sample of fluid;
    a one-way valve, disposed in the first conduit, that allows fluid to flow downstream towards the sampling chamber while preventing backflow of fluid from the sampling chamber;
    withdrawal means for enabling withdrawal of fluid from the sample chamber and,
    a gas vent with a filter in fluid communication with the sampling chamber, the gas vent for venting gas displaced by the sample.

22. The system according to claim 21, wherein the withdrawal means includes a hollow spike in fluid communication with the sample chamber, the hollow spike including a piercing end.

23. The system according to claim 22, wherein the piercing end is covered by a removable cap to prevent exposure and accidental damage.

24. The system according to claim 22, further comprising a first container capable of being pierced by the piercing end of the hollow spike.

25. The system according to claim 24, wherein the first container includes a septum and wherein the piercing end of the hollow spike is capable of piercing the septum.

26. The system according to claim 24, wherein the first container is evacuated prior to being pierced by the piercing end of the hollow spike.

27. The system according to claim 22, further comprising:
    a connector enabling fluid communication between the first conduit, the hollow spike, and the sample chamber.

28. The system according to claim 27, wherein the connector is a Y-connector.

29. The system according to claim 21, wherein the withdrawal means includes a second conduit in fluid communication with the sample chamber, the second conduit positioned downstream from the one-way valve.

30. The system according to claim 29, wherein the second conduit is closed at a first end, the first end capable of being attached to a first container by a sterile connection device.

31. The system according to claim 29, wherein the second conduit is coupled to a hollow spike, the hollow spike including a piercing end.

32. The system according to claim 29, further comprising:
    a connector, the connector enabling fluid communication between the first conduit, the second conduit, and the sample chamber.

33. The system according to claim 32, wherein the connector is a Y-connector.

34. The system according to claim 21, wherein the first conduit is sealed at a first end, the first end upstream from the one-way valve and capable of being attached to a second container by a sterile connection device.

35. The system according to claim 34, wherein the second container is a blood product bag.

36. The system according to claim 21, wherein the first conduit is in unitary construction with, and attached at a first end to, a second container, the first end upstream from the one-way valve.

37. The system according to claim 36, wherein the second container is a blood product bag.

38. The system according to claim 21, wherein the first conduit is in communication with the gas vent, the gas vent being positioned downstream from the one-way valve.

39. The system according to claim 21, wherein the sampling chamber includes indicia that indicates a predetermined volume of fluid within the sample chamber.

40. The system according to claim 21, wherein the sampling chamber includes indicia that indicates a volume of fluid downstream from the one-way valve.

41. The system according to claim 21, further comprising a clamp for controlling flow of fluid in the first conduit.

42. The system according to claim 21, wherein the sampling chamber is flexible and resilient.

43. The system according to claim 42, wherein the sampling chamber defines a pre-determined volume when in a resting state.

44. The system according to claim 42, wherein the sampling chamber is capable of being squeezed so as to expel fluid from the sampling chamber, and further released so as to create a vacuum for acquiring the sample fluid.

45. The system according to claim 44, wherein after being released, the sampling chamber returns to a predetermined volume.

46. The system according to claim 21, wherein the sampling chamber is made of a rigid material.

47. The system according to claim 21, wherein the one-way valve prevents backflow of at least one of air and liquid.

48. A method for obtaining a sample of a fluid from a fluid source, the method compromising:
    introducing the fluid through a first port in fluid communication with the fluid source;
    allowing the fluid to flow from the first port towards a sterile sampling chamber having a gas vent with a filter in fluid communication with the sampling chamber, while preventing backflow of fluid towards the first port; and
    withdrawing the fluid from the sampling chamber via a second port.

49. The method according to claim 48, further comprising testing the fluid withdrawn from the sampling chamber.

50. The method according to claim 49, wherein testing includes at least one of bacterial detection and cell counting.

51. The method according to claim 48, further comprising attaching a sample vial to a second port, the second port in fluid communication with the sampling chamber.

52. The method according to claim 48, wherein the first port is in unitary construction with, and attached to, the fluid source.

53. The method according to claim 48, wherein the first port is sealed, and wherein introducing the fluid includes attaching the first port to the fluid source using a sterile connection device.

54. The method according to claim 50, wherein attaching the first port to the fluid source source includes applying heat to the first port.

55. The method according to claim 54, wherein applying heat includes applying a radio frequency signal.

56. The method according to claim 48, wherein allowing the fluid to flow from the first port towards the sampling chamber while preventing backflow of fluid towards the first port includes providing a one-way valve positioned between the first port and the sampling chamber.

57. The method according to claim 48, wherein the sampling chamber is flexible and resilient, and wherein introducing the fluid into the first port includes squeezing the sampling chamber to create a vacuum, followed by releasing the sampling chamber to create a vacuum in the sampling chamber.

58. The method according to claim 57, wherein releasing the sampling chamber includes returning the sampling chamber to a predefined volume.

59. The method according to claim 48, further comprising venting the gas displaced from the fluid entering the sampling chamber.

60. The method according to claim 54, wherein the sampling chamber is in fluid communication with a vent, the method further comprising filtering the vent.

61. The method according to claim 48, wherein introducing the fluid into the first port includes opening a clamp that controls flow of fluid through the first port.

62. The method according to claim 48, wherein the sampling chamber includes indicia corresponding to a predetermined volume of fluid, and wherein introducing the fluid into the first port includes:
    comparing an amount of fluid entering the sampling chamber with the volume level indicated by the indicia; and
    stopping the flow of fluid through the first port upon fluid reaching the indicia.

63. The method according to claim 48, wherein the fluid source is a blood component bag.

64. The method according to claim 63, wherein the fluid is chosen from the group of fluids consisting of platelets, whole blood, red cells, and plasma.

65. The method according to claim 51 wherein the second port includes a hollow tube in fluid communication with the sampling chamber, the hollow tube including a piercing end, wherein the sample vial includes a septum, and wherein attaching the sample vial to the second port includes piercing the septum with the piercing end.

66. The method according to claim 51, wherein the second port is sealed, and wherein attaching the sample vial to the second port includes utilizing a sterile connection device.

67. The method according to claim 66, wherein attaching the sample vial to the second port includes applying heat to the second port.

68. The method according to claim 66, wherein applying heat includes applying a radio frequency signal.

69. The method according to claim 51, wherein the sample vial includes an evacuated volume forming a vacuum, the method further comprising drawing the fluid from the sample chamber into the sample vial due to the vacuum.

70. The method according to claim 51, further comprising squeezing the sample chamber to expel the fluid in the sample chamber into the sample vial.

71. A closed fluidic sampling system comprising:
    a first port for receiving a sample of fluid;
    a sampling chamber in fluid communication with the first port;
    a second port in fluid communication with the sampling chamber, the second port for withdrawing fluid from the sampling chamber and,
    a gas vent with a filter in fluid communication with the sampling chamber, the gas vent for venting gas displaced by the sample.

* * * * *